United States Patent [19]

Walinsky

[11] Patent Number: 5,575,771
[45] Date of Patent: Nov. 19, 1996

[54] BALLOON CATHETER WITH EXTERNAL GUIDEWIRE

[76] Inventor: Paul Walinsky, 8910 Carlisle Rd., Wyndmoor, Pa. 19038-7412

[21] Appl. No.: 427,748

[22] Filed: Apr. 24, 1995

[51] Int. Cl.⁶ ................................................ A61M 29/00
[52] U.S. Cl. .......................... 604/96; 604/93; 604/164; 604/264; 604/280; 606/194
[58] Field of Search ..................... 604/96–103; 606/191, 606/184, 192–195

[56] References Cited

U.S. PATENT DOCUMENTS

| | | |
|---|---|---|
| 4,581,017 | 4/1986 | Sahota . |
| 4,762,129 | 8/1988 | Bonzel . |
| 4,824,435 | 4/1989 | Glesy et al. . |
| 4,909,252 | 3/1990 | Goldberger . |
| 4,944,745 | 7/1990 | Sogard et al. . |
| 5,257,974 | 11/1993 | Cox . |
| 5,344,413 | 9/1994 | Allman et al. . |
| 5,383,853 | 1/1995 | Jung et al. . |
| 5,383,890 | 1/1995 | Miraki et al. . |
| 5,385,548 | 1/1995 | Williams et al. . |
| 5,395,332 | 3/1995 | Ressemann et al. . |
| 5,409,458 | 4/1995 | Khairkhahan et al. . |

OTHER PUBLICATIONS

Four-page Medtronic Advertisement For "Falcon" balloon catheter.

Primary Examiner—Randall L. Green
Assistant Examiner—Perry E. Van Over
Attorney, Agent, or Firm—William H. Meise

[57] ABSTRACT

A catheter (10) for use with a guidewire (40) includes an elongated, flexible body (12a) defining distal and proximal ends, and also defining a balloon inflation lumen (14) extending therethrough. A balloon (24) is affixed near the distal end, at a location selected so that an extending portion (12b) of the catheter extends distally beyond the balloon. A guidewire retaining arrangement (30) is located on an exterior part of the extending portion (12b) of the catheter, for allowing the catheter to slide relative to the guidewire, while being maintained adjacent thereto. In a particular embodiment of the invention, the balloon (24) has a perfusion channel (22) extending from a distal side (16) of the balloon to the proximal side. The perfusion channel may have walls which have different compliance than the remainder of the balloon. In an embodiment with a lobed balloon (724), the guidewire retaining arrangements are located so as to direct the guidewire between the lobes of the balloon.

18 Claims, 5 Drawing Sheets

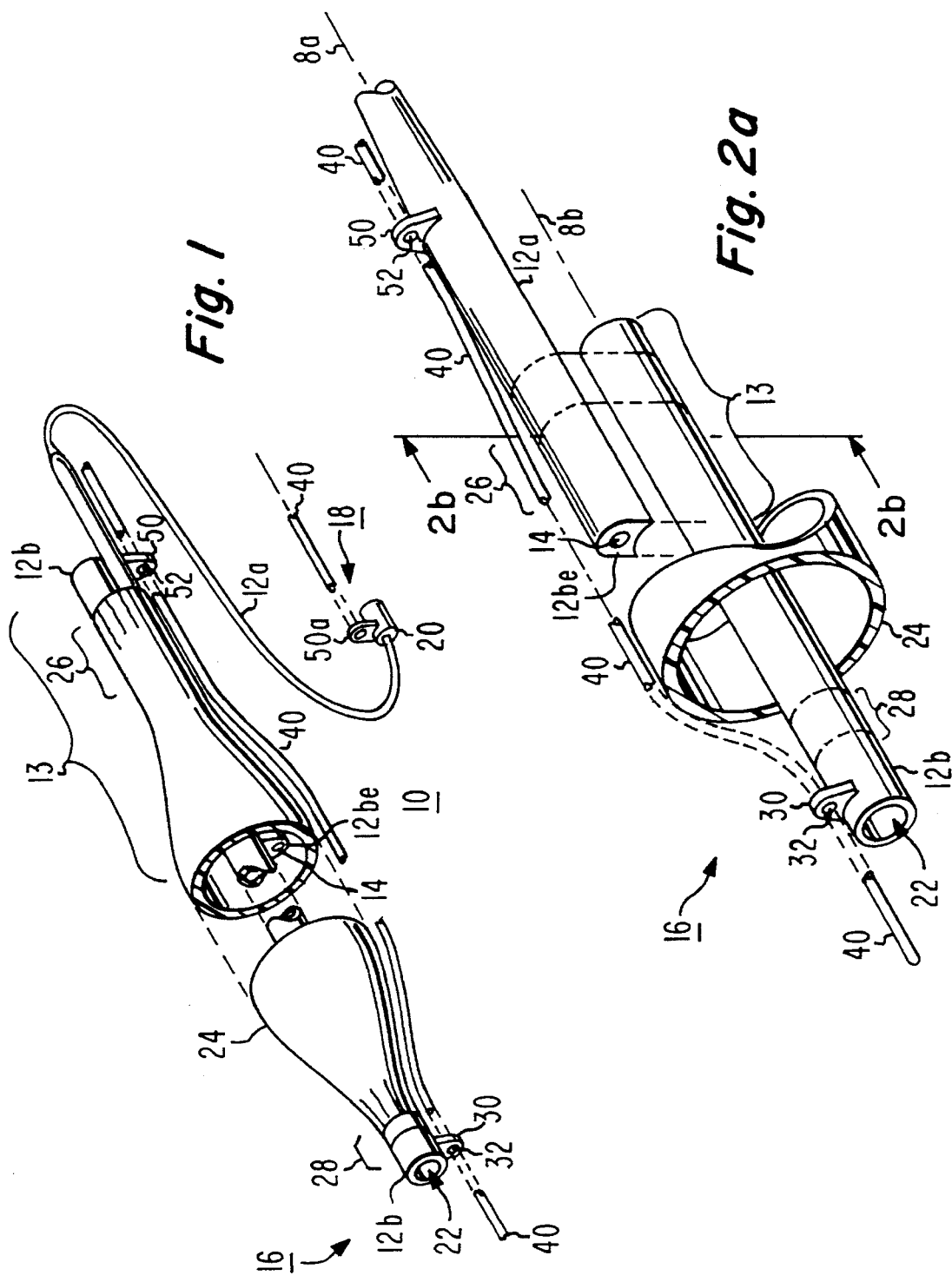

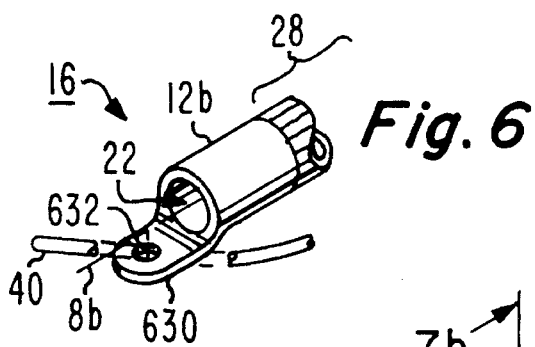
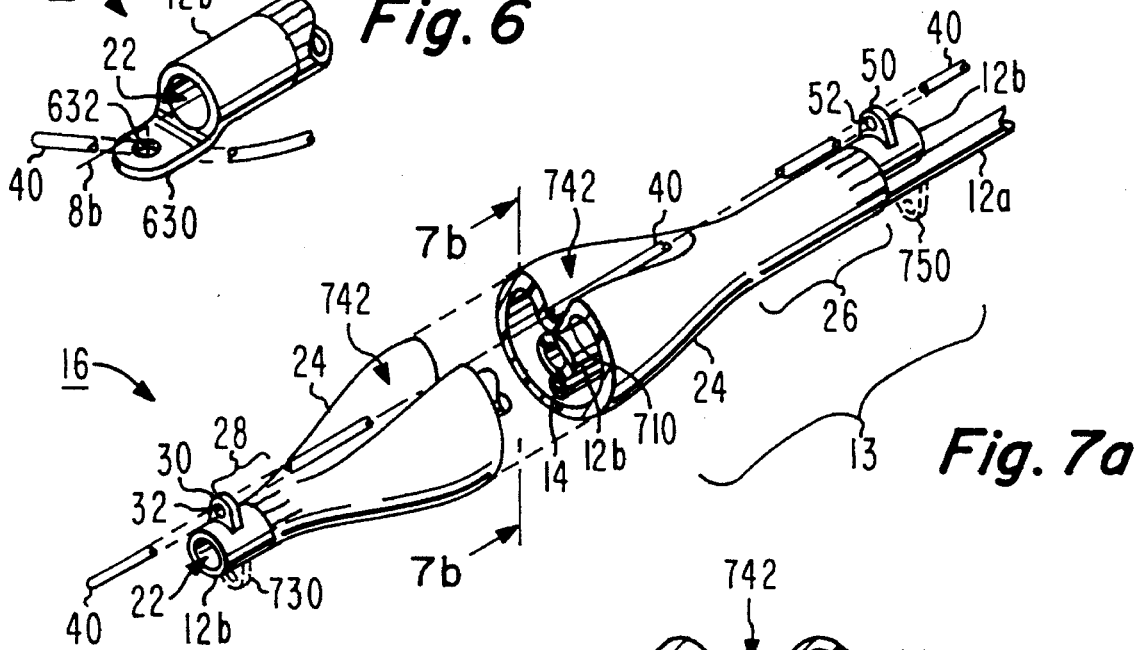
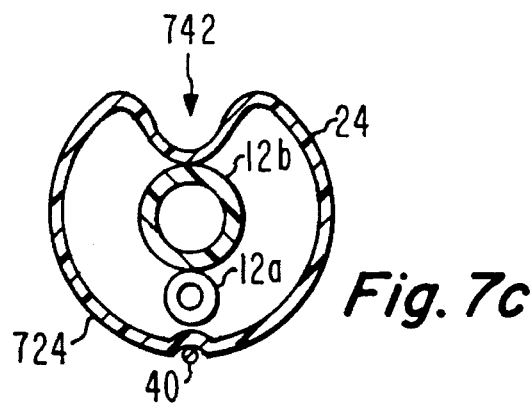
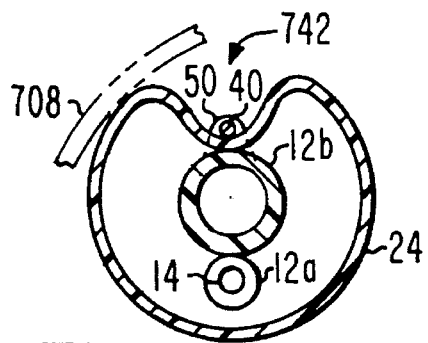
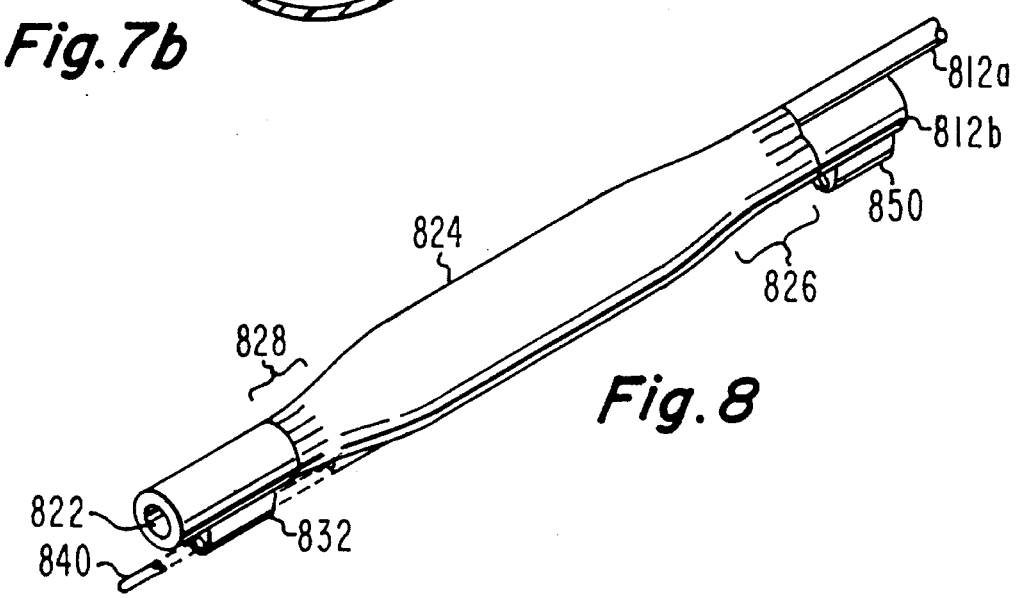

BALLOON CATHETER WITH EXTERNAL GUIDEWIRE

FIELD OF THE INVENTION

This invention relates to balloon catheters for coronary angioplasty which are adapted for use with guidewires, and especially to such perfusion balloon catheters.

BACKGROUND OF THE INVENTION

The heart muscle is nourished by blood flow through coronary arteries. These arteries are quite small, but are vital for carrying the blood flow required to maintain the heart in a healthy condition. A predisposing cause of coronary disease is the accumulation of atherosclerotic plaques on the interior walls of the coronary arteries, which tends to reduce their effective diameter. When the lumen is sufficiently narrowed, the rate of blood flow therethrough may be so diminished that spontaneous formation of a thrombus or clot occurs. Once a blood clot has begun to form, it extends within minutes into the surrounding blood, as mentioned in U.S. Pat. No. 4,643,186, issued Feb. 17, 1987, in the names of Rosen and Walinsky, and may, effectively block coronary blood flow. Thus, it is important to restore coronary blood flow before thrombosis occurs. Coronary bypass surgery can ameliorate the effects of such blockage, but may be undesirable, in part because it requires invasive surgery.

Balloon angioplasty techniques are less invasive than coronary artery bypass surgery, and have been shown to be effective under some conditions. In general, a balloon angioplasty procedure is performed by obtaining access to the interior of the affected coronary artery, and advancing a deflated balloon to the location of the stenosis. The balloon is inflated by applying fluid pressure through an inflation/deflation ("inflation") lumen of the catheter, to thereby apply balloon pressure tending to expand the lumen of the coronary artery, to thereby press the plaque against the walls of the coronary artery, and to expand the walls of the artery. When the stenotic portion of the lumen of the blood vessel or coronary artery has about the same diameter as adjacent portions which are free from plaque, the procedure may be terminated, the balloon deflated and the catheter removed. It has been observed, as in the article entitled "Perfusion During Coronary Angioplasty," by Rossen, published at pages 103–106 in the June, 1989 issue of Cardio, that increased time with the balloon inflated is associated with an improved result. When the balloon is removed, the artery tends to remain open, allowing for increased blood flow.

The art relating to angioplasty includes many advances, such as the microwave-aided angioplasty described in the above-mentioned Rosen and Walinsky patent, reduced diameters as described in an article entitled "The Balloon On A Wire Device" by Myler et al, published at pages 135–140 of Volume 14, Nov. 2, 1988 of the periodical "Catheterization and Cardiovascular Diagnosis," published by Alan R. Liss, and various configurations of guide wires and catheter lumens, described for example in "Selection or Dilatation Hardware for PCTA-1985" by Topol et al., published at pages 629–637 of Volume 11, Nov. 6, 1985 of the aforementioned periodical.

Those portions of the heart muscle supplied with blood flow through the artery being treated during balloon angioplasty are partially deprived of blood flow when the catheter with deflated balloon is being positioned in the stenotic region, and may be completely deprived of blood flow when the balloon is inflated. This in turn has a tendency to decrease heart pumping efficiency, and the blood pressure tends to drop. Chest pains result in some patients. Either of these indications may undesirably require early termination of the procedure. Dilatation catheters are available, as mentioned in the above-mentioned Rossen article, in which perfusion or blood flow past the occluding catheter and balloon is provided by fenestrations or apertures into the distal lumen of the catheter on both sides of the balloon. When the distal lumen is also used for a guide wire, as in U.S. Pat. No. 4,762,129, issued Aug. 9, 1988 in the name of Bonzel, and in U.S. Pat. No. 4,994,745, issued Jul. 31, 1990, in the name of Sogard et al., the guide wire blocks at least a portion of the perfusion channel, and must be retracted during perfusion. This retraction requires additional manipulation, and may result in loss of position of the balloon. Further manipulation is required if the guide catheter surrounding the dilatation catheter must also be retracted. Such perfusion catheters tend to be somewhat larger in diameter and stiffer than conventional catheters having the same inflated balloon diameter, and are therefore more difficult to position. Also, their larger diameter excludes their use in the small arteries into which conventional angioplasty balloon catheters may fit.

Perfusion balloon catheters are described in U.S. Pat. No. 4,909,252, issued Mar. 20, 1990 in the name of Goldberger, and in U.S. Pat. No. 5,108,370, issued Apr. 12, 1992 in the name of Walinsky, in which the perfusion channel extends through the balloon, and the guidewire extends through a separate lumen. These balloon catheters provide a perfusion path which is independent of the guidewire, so that the amount of manipulation is reduced by eliminating the need to remove the guidewire to allow sufficient perfusion during balloon inflation, and reduces the possibility of losing balloon position by the removal of the guide wire.

Differential compliance of the balloon material is described in U.S. patent application Ser. No. 08/279,061, filed Jul. 22, 1994, in the name of Walinsky. The differential compliance aids in preventing closure of the perfusion channel extending through the balloon as the balloon is inflated. The differential compliance may require thicker balloon material adjacent the perfusion channel. The various improvements to balloon catheters has tended to increase the diameter of the catheter in the region of the collapsed balloon, which tends to reduce their usefulness in smaller coronary arteries. Improved balloon catheters are desired.

SUMMARY OF THE INVENTION

In balloon angioplasty catheters according to the invention, the overall diameter of the balloon catheter, in the region of the balloon, is reduced by eliminating a separate guidewire lumen, and the blockage of the perfusion channel, or the additional manipulation required to remove the guidewire from the perfusion channel, occasioned by using the perfusion channel to house the guidewire, is eliminated by running the guidewire outside the balloon.

A catheter adapted for use with a guidewire having a particular diameter comprises an elongated, flexible body defining a distal end and a proximal end, and also defining a balloon inflation lumen extending from a location near the proximal end of the body to a location near the distal end of the body. A balloon is affixed at a location near the distal end of the body, with the interior of the balloon in communication with the balloon inflation lumen. The location is selected so that an extending portion of the catheter extends distally beyond the expansible portion of the balloon. A guidewire retaining arrangement is located on an exterior part of the extending portion of the catheter, and is dimensioned for allowing the extending portion to slide relative to the guidewire, while being maintained adjacent thereto. In a particular embodiment of the invention, the balloon defines a perfusion channel extending from a distal side of the balloon to a proximal side of the balloon. The perfusion channel may have walls which have different compliance than the remainder of the balloon. In one embodiment of the invention, the retaining arrangement comprises a loop defining an aperture, and the diameter of the aperture is no less than the diameter of the guidewire. In an embodiment with a lobed balloon, the guidewire retaining arrangements are located so as to direct the guidewire between the lobes of the balloon.

A method for performing balloon angioplasty according to the invention includes the step of introducing a guidewire into a coronary artery requiring angioplasty, while maintaining a particular length of said guidewire outside the body. According to the method, a balloon angioplasty catheter is procured, which has a total length greater than the particular length of the guidewire, and having a guidewire retention loop located distal to the expansible portion of the balloon, on the exterior of the balloon catheter. The guidewire retention loop of the balloon catheter is threaded onto the proximal end of the guidewire extending outside the patient. The distal end of the balloon catheter, with its guidewire retention loop, is then advanced along the guidewire, as a result of which the guidewire lies along the exterior of the balloon. When the balloon catheter is in position for angioplasty, the balloon is inflated, thereby pressing the guidewire against the wall of the coronary artery. In a particular method, the catheter is a perfusion catheter having no lumen through which the guidewire passes.

DESCRIPTION OF THE DRAWINGS

FIG. 1 is a simplified perspective or isometric view of a catheter according to the invention, partially cut away to illustrate interior details;

FIG. 2a is an exploded, partially cut away view of the arrangement of FIG. 1.

FIG. 6 is a simplified isometric or perspective view of another type of guide-wire retainer which can be used instead of the one illustrated in conjunction with FIGS. 1 and 2a;

FIG. 7a is a simplified perspective or isometric view, partially cut away to reveal interior details, FIG. 7b is a cross-section of the arrangement of FIG. 7a, and FIG. 7c is a cross-section of an alternative embodiment similar to that of FIG. 7a;

FIG. 8 is a simplified perspective or isometric view of the distal end of a catheter according to the invention, illustrating elongated guide-wire retainers;

DESCRIPTION OF THE INVENTION

Figure 2B:
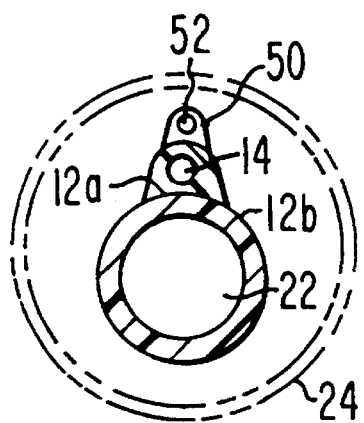
FIG. 2b is a cross-section thereof.

In FIG. 1, a catheter designated generally as 10 includes an elongated, flexible body 12a, defining a balloon inflation lumen 14, a distal end 16, and a proximal end 18. A balloon inflation fluid connector 20 is illustrated as being affixed to the proximal end 18 of body 12a of catheter 10.

At the distal end 16 of catheter 10 of FIG. 1, body 12a is affixed to or joins a second portion 12b of the catheter, which extends distally from the distal end 12be of body portion 12a, as illustrated in more detail in FIG. 2a. The region in which the joinder occurs is designated 13, and the local axis 8a of body portion 12a lies parallel to the local axis 8b of body portion 12b. Distal body portion 12b may or may not be more rigid than flexible body portion 12a, and it defines a perfusion passage or bore 22. A balloon membrane (balloon) 24 surrounds body portions 12a and 12b. Balloon membrane 24 has greater compliance than body portion 12a or 12b, and is affixed, at the proximal end of balloon 24, to the junction of catheter body members 12a and 12b, forming a fluid-tight seal in the region designated 26, which is in the overlap of the two body portions. At the distal end of balloon 24, its membrane is collected about, and affixed in a fluid-tight sealing manner, to a portion 28 of perfusion body member 12b. Thus, the open end of balloon inflation lumen 14 of elongated catheter body portion 12a at its distal end 12be lies in the interior of balloon 24, so balloon inflation fluid may be added to or extracted from the interior of balloon 24 by way of fluid connector 20. Thus, balloon 24 can expand in a region between its attachment regions 26 and 28, which are non-expansible. The ends of perfusion channel 22 are open beyond the distal and proximal ends of the expansible or inflatable portion of the balloon.

According to an aspect of the invention, a guidewire guide or retainer 30 is located on perfusion body portion 12b at a location, such as the location illustrated in FIGS. 1 and 2a, which is selected to be more distal than the inflatable portion of balloon 24. In general, this will be a location which is more distal than the region 28 at which the balloon membrane 24 is sealingly fastened to perfusion body portion 12b, but the sealing connection could, if desired, extend more distally than guide or retainer 30, so long as the actual guidewire aperture 32 is not within the expansible portion of the balloon. The retainer 30 may be in the form of a loop, or, as described below, in the form of an elongated channel.

The dimensions of guidewire aperture 32 are selected to provide a sliding fit with a particular guidewire. Ordinarily, catheters are provided without guidewires, and guidewires are provided in particular sizes as a separate item. Common guidewire sizes are 0.010, 0.014, 0.016, and 0.018 inch diameter. Prior-art catheters have their guidewire lumens made to accommodate one of these sizes, which of course means that they will accommodate all smaller sizes.

The location of guidewire retainer 30 relative to balloon 24 as illustrated in FIGS. 1 and 2a is advantageous, by virtue of allowing "monorail" type manipulation of the catheter, and also by virtue of avoiding the need for a discrete lumen to house the guidewire in the balloon region. This, in turn results in a diminished cross-sectional area of the catheter in the balloon region, so that the collapsed balloon of the catheter can have a smaller diameter than in the prior art, without any blockage of the perfusion passage, and without requiring additional manipulation to retract the guidewire from the perfusion passage. The illustrated location of guidewire retainer 30 has the effect of causing the catheter guide wire, illustrated as 40 in FIGS. 1 and 2a, to extend over the exterior of the balloon when the balloon is inflated. While the presence of the guidewire 40 adjacent to the exterior of the balloon 24 may reduce the cross-sectional area of the balloon when it is inflated within a vas, it does not affect the cross-sectional area of the perfusion passage 22.

In addition to the guidewire retainer 30 on the perfusion portion 12b of the catheter, at a location more distal than the expansible portion of the balloon 24, it may be advantageous to have additional guidewire retainers at locations more proximal than the expansible portion of the proximal end of the balloon. One such additional retainer is illustrated as 50 in FIGS. 1 and 2a, and it is located on elongated body portion 12a, near the proximal portion of body portion 12b. Retainer 50 includes an aperture 52, which may be dimensioned to clear a particular size of guidewire, as discussed above. Other guidewire retainers may be used along the length of elongated catheter body portion 12a, and near the proximal end thereof, such as retainer 50a in FIG. 1.

While the guidewire retainers 30, 50 effectively increase the diameter of the catheter 10 at those locations at which they occur, this increase in diameter is not important, because the body portions 12a, 12b are smaller in diameter than the collapsed balloon. However, according to the invention, no guidewire retainers occur along the length of the catheter at which the expansible portion of the balloon occurs, because they would undesirably increase the effective diameter of the catheter at that important location. Similarly, the guidewire does not pass through a discrete lumen at a location along the length of the catheter at which an expansible portion of the balloon occurs.

FIG. 2b illustrates a cross-section of the arrangement of FIGS. 1 and 2a at cross-section 2b—2b of FIG. 2a, and illustrates a circular balloon inflation lumen 14. FIG. 2b also illustrates that the cross-section of body portion 12a may be curved to match the curvature of body portion 12b in joinder region 13, to provide an improved (larger) adhesion area. In FIG. 2b, the location of guidewire retainer 50 may be misunderstood as effectively increasing the overall cross-section of the catheter, but as mentioned above, the location of retainer 50 is away from the region with the balloon, and thus does not contribute to the diameter at the critical region.

Figure 3:
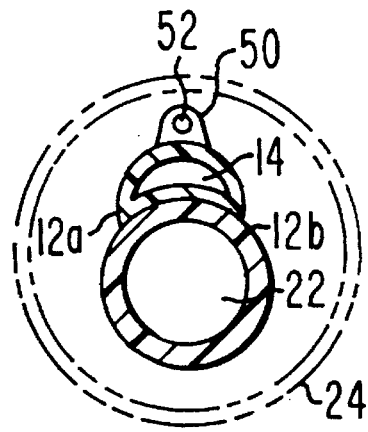
FIG. 3 is a cross-section of a catheter similar to that of FIG. 2b, in which the balloon inflation lumen is differently shaped.

FIG. 3 is similar to FIG. 2b, but illustrates a modification of the shape of the balloon inflation lumen 14 to provide more cross-sectional area, and thereby a lesser resistance to the flow of balloon inflation fluid.

Figure 4:
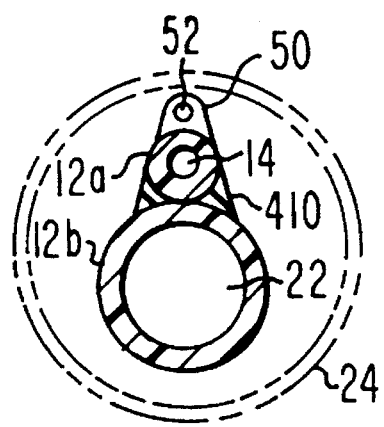
FIG. 4 is a cross-section of a catheter similar to that of FIG. 2b, in which the main body of the catheter is differently shaped.

FIG. 4 illustrates the use of circular cross-sectional shapes for both elongated body portion 12a and perfusion body portion 12b, which has a tendency to prevent formation of a good seal to the balloon membrane at the sealing region 26 of FIGS. 1 and 2a. This is readily solved by the use of an additional amount of sealing material, illustrated as 410 in FIG. 4, added at the time that the balloon membrane is sealed to the sealing region 26, which fills in the slight gaps. These catheters are so small that the additional amount of adhesive required for sealing two round tubes is insignificant.

Figure 5:
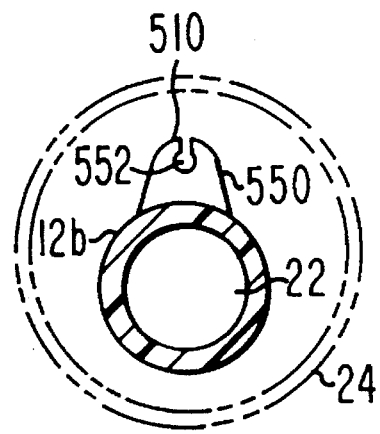
FIG. 5 is a cross-section of another embodiment of the invention, in which the guide-wire retainer can snap onto the guide wire.

FIG. 5 illustrates an alternative form of a guidewire retainer 550, which may be used in place of any or all of those discussed above. Guidewire retainer 550 includes an aperture 552 which is selected to clear the appropriate guidewire, and also includes a slot 510 extending from the aperture 552 to the exterior. The arrangement allows the retainer to be affixed to the guidewire without the guidewire having to be threaded into the aperture, but the aperture may be affixed along the length of the guidewire by "snapping" the slot over the guidewire, and relying on the compliance or elasticity of the material of the retainer to close the slot around the guidewire.

FIG. 6 illustrates yet another type of guidewire retainer which may be used at the distal end of the catheter. In FIG. 6, perfusion portion 12b of the catheter body has most of the material cut away or notched at its distal end, leaving a "tab" 630 protruding distally from the end of the cut-away material. Tab 630 lies in, or tangent to a plane which is perpendicular to a radial from axis 8b, and defines an aperture 632, which is preferably oval or elongated, to allow guidewire 40 to pass through at an angle. Naturally, guidewire 40 may pass through aperture 632 as illustrated from the bottom side of the aperture, or it may instead pass through the upper side of the aperture.

FIGS. 7a and 7b illustrate an arrangement similar to that of FIG. 1, but in which the balloon 24 is attached to perfusion body portion 12b along an elongated line 710 of adhesion, which results in formation of a balloon lobe 724 when the balloon is inflated; the region where the balloon lobe cannot expand, because of the attachment to the perfusion body portion 12b, is designated as a further perfusion portion or channel 742. Perfusion channel 742 is defined by the wall of balloon 24 in conjunction with the adjacent wall of the coronary artery, part of which is illustrated in phantom as 708 in FIG. 7b. With the retainers 30 and 50 located and circumferentially aligned with the channel (only guidewire retainer 50 illustrated in FIGS. 7a and 7b), the guidewire lies in further perfusion portion 742. While this may be desirable in some circumstances, retaining the guidewire 40 by the alternate locations for the guidewire retainers, which alternate locations are illustrated in phantom and are designated 730 and 750, results in the position of the guidewire 40 relative to the inflated balloon lobe 724 which is illustrated in FIG. 7c. In FIG. 7c, the guidewire runs along the outside of the inflated balloon, and does not take up any cross-section within the perfusion channels. If the guidewire is to be directed through the perfusion portion of the balloon lobe, the balloon may have plural lobes and plural perfusion channels defined thereby, and the guidewire may extend through one of the channels defined thereby.

In FIG. 8, the distal end of a catheter includes the distal portion of the elongated body 812a, affixed to a perfusion portion 812b, with a perfusion bore 822. A balloon 824, illustrated in its deflated or collapsed state, is sealingly affixed to perfusion portion 812b in a region 828, and to both body portion 812a and perfusion portion 812b in a region 826. As in the case of the other catheters, body portion 812a defines a balloon inflation lumen (not visible in FIG. 8) which opens into the balloon. An elongated channel 832 located on perfusion portion 812b distal from the fastening of balloon 824 is dimensioned to accommodate and retain the guidewire, illustrated in phantom. A similar elongated channel 850, located on perfusion portion 812b proximal to balloon sealing region 826, provides corresponding retention.

Figure 9:
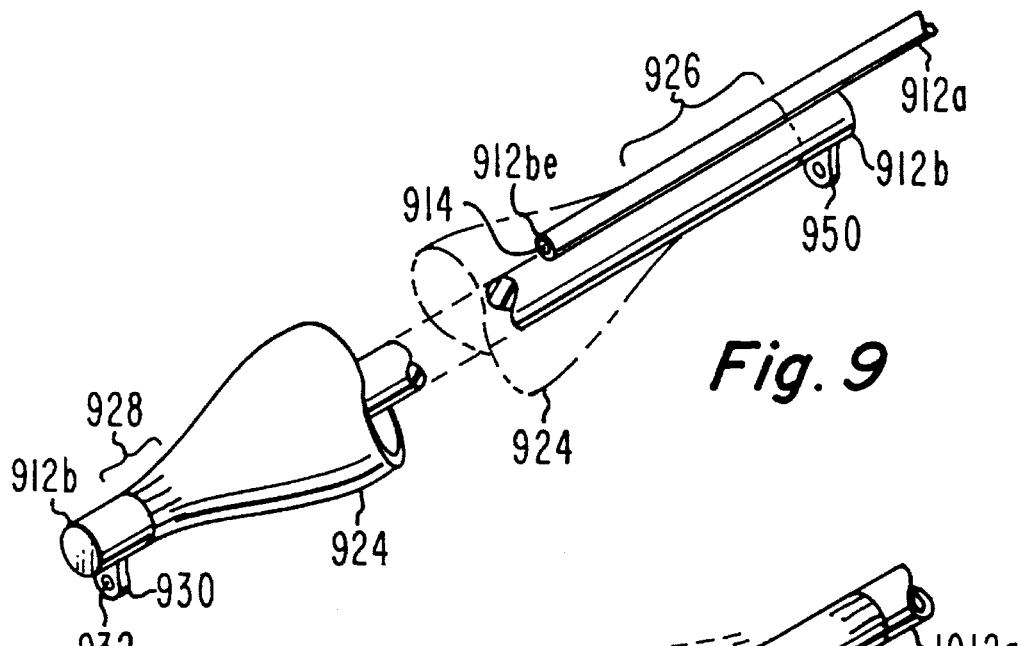
FIG. 9 is a simplified perspective or isometric view of the distal end of a catheter according to the invention, illustrating a non-perfusion balloon catheter according to the invention.

FIG. 9 illustrates a non-perfusion balloon catheter similar to that of FIG. 1. In FIG. 9, the catheter includes an elongated, flexible body portion 912a defining a balloon inflation lumen 914, which opens into the balloon 924 at a distal end 912be. A solid (non-perfusion) extending portion 912b of the catheter is affixed to the distal end of body portion 912a at region 926, and extends distally therefrom. Near the distal end of portion 912b, balloon 924 is sealingly affixed thereto in a region 928. Balloon 924 is also sealingly affixed to body portion 912a and extending portion 912b in region 926. According to the invention, the extending portion 912b bears a guidewire retention loop 930, with an aperture 932, distal from the expansible portion of the balloon. Similarly, that portion of the extending portion 912b which is proximal to the expansible portion of the balloon, which may be, for example, proximal to sealing region 926, has another guidewire retention loop 950. Naturally, loops 932 and 950 may be elongated channels as in FIG. 8, or they may be slotted, as in FIG. 5.

In use of the catheters according to the invention, the guidewire may be inserted into the body, to the correct position, as, for example, by use of a guide catheter. The most distal guidewire retention loop or channel of the angioplasty balloon catheter is then threaded over the proximal end of the guidewire, and the distal end of the angioplasty balloon catheter can then be slid along the guidewire into the proper position. If there are additional guidewire retention loops or channels more proximal from the first on the angioplasty balloon catheter, these are also threaded onto the guidewire as they reach the appropriate position. This arrangement has the great advantage that the length of the guidewire needs to be only long enough to extend slightly beyond the body of the patient when it is in position, as the angioplasty balloon catheter can be slid over the end of the guidewire, while still having a portion of the guidewire to hold onto, to keep it in the proper position. Otherwise, the guidewire would have to extend outside the patient by more than the full length of the angioplasty balloon catheter. Additionally, since the guidewire does not pass through the balloon, but rather outside the balloon, no additional lumen is needed, thereby reducing the total diameter of the catheter, which is very important, especially in the region of the balloon, so that a balloon catheter according to the invention may be smaller than a conventional balloon catheter in which the guidewire passes through the balloon. A smaller diameter allows the catheter to be used in smaller coronary arteries.

Figure 10A:
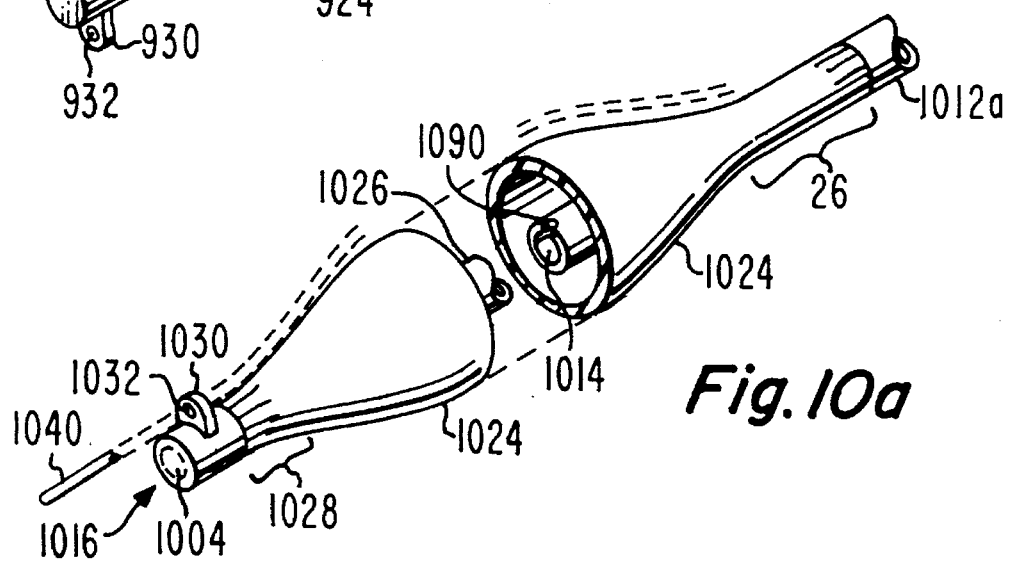
FIG. 10a is a simplified perspective or isometric view of the distal end of a catheter according to the invention, illustrating another non-perfusion balloon catheter according to the invention.

FIG. 10a illustrates a non-perfusion angioplasty catheter according to the invention, in which the portion of the catheter extending beyond the balloon is contiguous with the elongated portion. More particularly, in FIG. 10a, flexible, elongated body 1012a defines a balloon inflation lumen 1014. Inflation lumen 1014 communicates to the interior of a balloon 1024, which is illustrated partially cut away to reveal interior details, by way of an aperture 1090, also seen partially cut away. Balloon 1024 is sealingly affixed to body portion 1012a at a location 1026 proximal from the inflatable portion of the balloon, and is similarly affixed to a portion 1012b of the body which extends distally from aperture 1090. At the extreme distal end of extension of balloon inflation lumen 1014, which would otherwise extend to extreme distal end 1016, a plug 1004 is sealingly affixed within the end of the lumen. The plug may be a wire, or it may be a hardened plug of adhesive. A guidewire retaining loop 1030, with aperture 1032, is affixed to the exterior of extending body portion 1012b, distal to the region in which the balloon can expand. As illustrated, the retaining loop 1030 is located distal to sealing region 1028. As with all the other guidewire retaining loops, the dimensions of guidewire retaining loop aperture 1032 are selected to accommodate the particular guidewire 1040 to be used. Additional guidewire retaining loops or channels may be used proximal to the balloon, as desired.

Figure 10B:
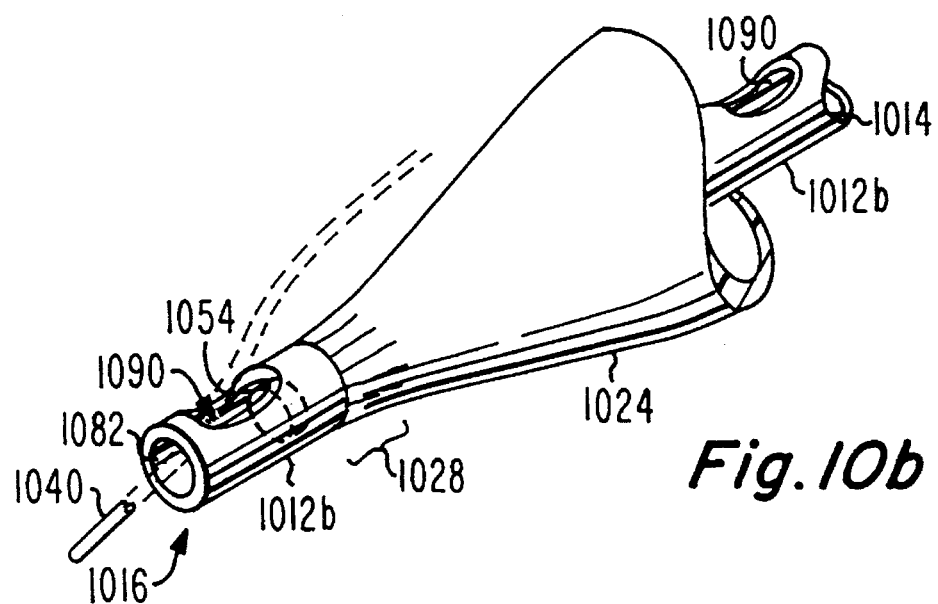
FIG. 10b is a detail illustrating a variant thereof.

FIG. 10b illustrates a variant of the arrangement of FIG. 10a, in which the distal end of balloon 1024 is affixed to a portion 1012b of the body which extends distally from the balloon attachment region 1028. Near the distal end of extension of balloon inflation lumen 1014, which would otherwise extend to extreme distal end 1016, a plug 1054 is sealingly affixed within a portion of the lumen. The plug may, of course, be a wire or a hardened plug of adhesive. At a location distal from plug 1054, an aperture 1090 is formed by notching the side of extension 1012b, exposing the lumen. This effectively forms the balloon inflation lumen into a guidewire 1040 retention loop 1082 at the extreme distal end of the catheter, without affecting the balloon inflation function, which occurs at locations more proximal than the extreme end of the catheter. Additional guidewire retaining loops or channels may be used proximal to the balloon, as desired.

Figure 11A:
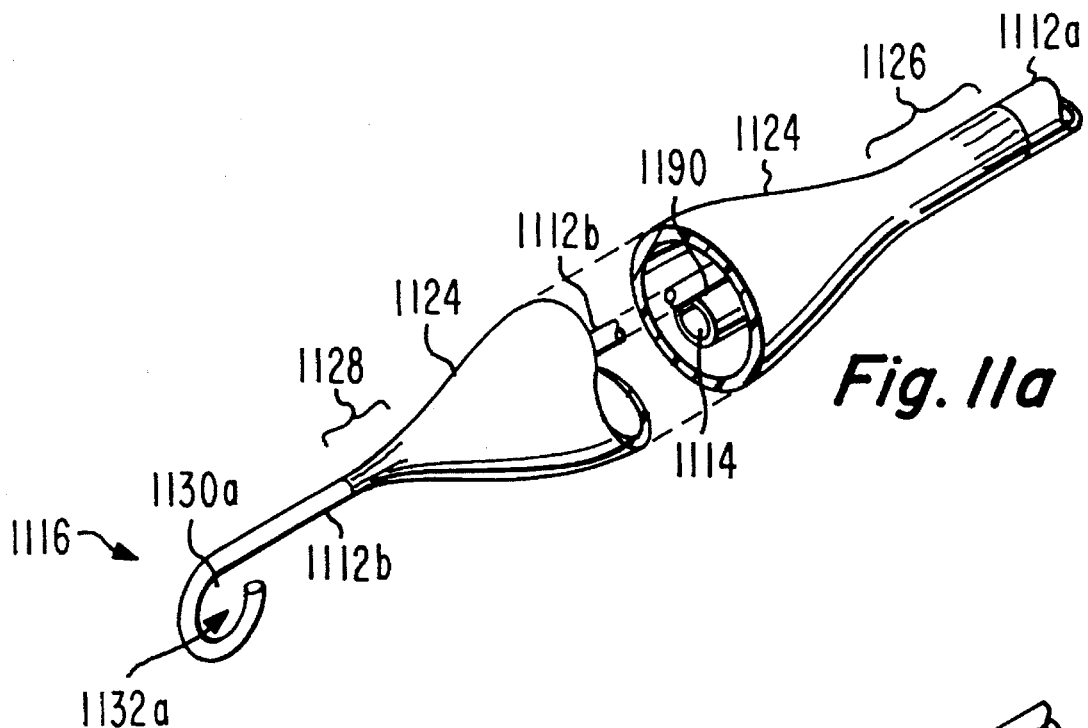
FIG. 11a is a simplified, perspective or isometric view, partially cut away to illustrate interior details, of a catheter according to the invention, in which the distally extending portion of the body is skeletonized.
Figure 11B:
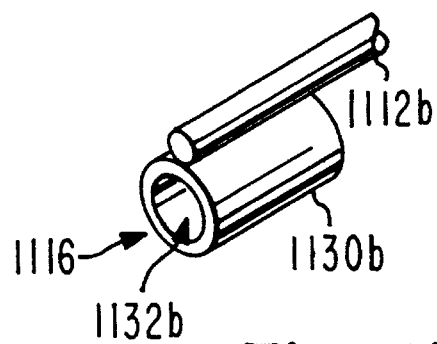
FIG. 11b illustrates an elongated guidewire retention channel attached at the distal end of the skeletonized body portion of FIG. 11a, and FIG. 11c illustrates a skeletonized guidewire retention channel.
Figure 11C:
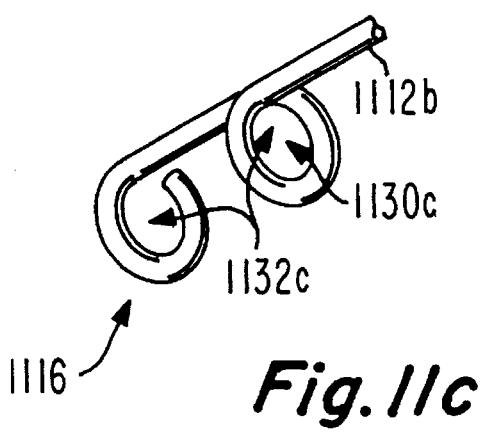

FIG. 11a is a simplified, perspective or isometric view, partially cut away to illustrate interior details, of a catheter according to the invention, in which the distally extending portion 1112b of the body is skeletonized to a simple wire. In FIG. 11a, an elongated, flexible portion 1112a of the catheter defines a balloon inflation lumen 1114, which terminates within the confines of balloon 1124. A distally extending body portion 1112b is attached at a region 1190 to body portion 1112a, and extends distally to the extreme distal end 1116. Balloon 1124 is sealingly attached to body portion 1112a at a region 1126, and is likewise attached to skeletonized body portion 1112b in a region 1128. The extreme distal end of skeletonized body portion 1112b is twisted to form a loop 1130a with an aperture 1132a dimensioned to accommodate a guidewire (not illustrated in FIG. 11a). FIG. 11b illustrates an elongated guidewire retention channel 1130b defining a guidewire retention channel 1132b attached at the distal end of skeletonized body portion 1112b instead of the twist 1130a. FIG. 11c illustrates a skeletonization of the elongated channel of FIG. 11b, in which the skeletonized distally extending body portion 1112b is twisted into two loops 1130c, which define two spaced-apart axially aligned apertures 1132c.

Other embodiments of the invention will be apparent to those skilled in the art. For example, instead of curving body portion 12a in the joinder region 13 where it attaches to body portion 12b, body portion 12b may be curved to match body portion 12a. As a further alternative, body portions 12a and 12b may be formed as an integral part, thereby eliminating the need for an adhesive connection. While the cross-sectional shapes have been illustrated as preformed before adhesive sealing in FIGS. 2b and 3, these shapes might be made by starting with round cross-sections, and by use of heat and pressure to result in molding the tubes together, so that they conform to each other in the joinder region.

What is claimed is:

1. A balloon catheter adapted for use with a guidewire, said catheter comprising:

an elongated, flexible body defining a distal end and a proximal end, and also defining a balloon inflation lumen extending from a location near said proximal end of said body to a location near said distal end of said body;

an extending portion of said body extending distally from said elongated, flexible body;

a balloon including an expansible portion, said balloon being affixed at a location near said distal end of said body, with the interior of said balloon in communication with said balloon inflation lumen, said location being selected so that said extending portion of said catheter extends distally beyond said expansible portion of said balloon; and guidewire retaining means located on said extending portion of said catheter, said retaining means being dimensioned for allowing said extending portion to slide relative to said guidewire, while being maintained adjacent thereto;

wherein said balloon includes a perfusion channel extending through said balloon from a distal side of said balloon to a proximal side of said balloon, and said perfusion channel does not extend though said body of said catheter.

2. A catheter according to claim 1, wherein said perfusion channel has walls which have lesser compliance than the remainder of said balloon.

3. A catheter according to claim 1, wherein said retaining means comprises a loop defining an aperture, the diameter of said aperture being no less than the diameter of said guidewire.

4. A catheter according to claim 1, wherein said extending portion of said catheter is skeletonized.

5. A balloon catheter adapted for use with a guidewire, comprising:

an elongated, flexible body defining a distal end and a proximal end, and also defining a balloon inflation lumen extending from a location near said proximal end of said body to a location near said distal end of said body;

a skeletonized extending portion of said body extending distally from said elongated, flexible body;

a balloon including an expansible portion, said balloon being affixed at a location near said distal end of said body, with the interior of said balloon in communication with said balloon inflation lumen, said location being selected so that said extending portion of said catheter extends distally beyond said expansible portion of said balloon; and guidewire retaining means located on said extending portion of said catheter, said retaining means being dimensioned for allowing said extending portion to slide relative to said guidewire, while being maintained adjacent thereto;

wherein said extending portion of said catheter is a wire.

6. A catheter according to claim 5, wherein said guidewire retaining means comprises a loop formed in said wire.

7. A catheter according to claim 1, wherein said guidewire retaining means comprises a notch in the wall of said perfusion channel distal to said balloon.

8. A catheter including a perfusion portion defining a channel for the flow of fluids, said catheter being adapted for use with a guidewire, said catheter comprising:

an elongated, flexible body defining a distal end and a proximal end, and also defining a balloon inflation lumen extending from a location near said proximal end of said body to a location near said distal end of said body;

a balloon including an inflatable portion affixed at a location near said distal end of said body, with the interior of said inflatable portion of said balloon in communication with said balloon inflation lumen, said location being selected so that said perfusion portion of said catheter extends through said balloon, and distally beyond said inflatable portion of said balloon, but not through said body of said catheter; and guidewire retaining means supported on said perfusion portion of said catheter at a location more distal than said inflatable portion of said balloon, said retaining means being dimensioned for allowing said perfusion portion to slide relative to said guidewire, while being maintained adjacent thereto.

9. A catheter according to claim 8, wherein:

said perfusion portion of said catheter comprises a tube including distal and proximal perfusion apertures, said tube being affixed to said body at a junction extending along a proximal portion of the length of said tube and a distal portion of the length of said body, with said distal and proximal perfusion apertures outside said expansible portion of said balloon.

10. A catheter according to claim 9, wherein:

said guidewire retaining means is affixed to an exterior portion of said tube at a location more distal than said inflatable portion of said balloon.

11. A catheter according to claim 9, wherein:

said guidewire retaining means comprises a loop contiguous with an outer surface of said tube.

12. A catheter according to claim 9, wherein said retaining means comprises a notch in the wall of said perfusion channel distal to said balloon.

13. A catheter according to claim 9, wherein:

said tube has a circular cross-section defining an axis, and wherein said axis of said tube extends parallel to the direction of elongation of the distal end of said body: and wherein said balloon is affixed to said body and to said tube at said junction, and is affixed to said tube at a location more distal than said junction.

14. A catheter according to claim 13, wherein said guidewire retaining means comprises a loop contiguous with an outer surface of said tube.

15. A catheter according to claim 15, wherein said loop defines a plane which is perpendicular to a radius extending from said axis of said tube.

16. A catheter according to claim 8, wherein said perfusion portion is a channel defined, in part, by a lobe of said balloon.

17. A catheter according to claim 15, wherein said guidewire retaining means is circumferentially aligned with said channel.

18. A catheter according to claim 16, wherein said guidewire retaining means is circumferentially aligned with said channel, whereby the guidewire lies along said channel defined by said lobe of said balloon.

* * * * *